US00PP08644P

United States Patent [19]

Button et al.

[11] Patent Number: Plant 8,644

[45] Date of Patent: Mar. 15, 1994

[54] ANTHURIUM PLANT NAMED PINK FROST

[75] Inventors: Richard J. Button, 1245 Obisbo Ave., Coral Gables, Fla. 33134; Ann E. Lamb, Lake Placid, Fla.

[73] Assignee: Richard J. Button, Coral Gables, Fla.

[21] Appl. No.: 34,822

[22] Filed: Mar. 12, 1993

[51] Int. Cl.[5] ..... A01H 5/00

[52] U.S. Cl. ..... Plt./88.1

[58] Field of Search ..... Plt. 88.1

*Primary Examiner*—James R. Feyrer

*Attorney, Agent, or Firm*—Foley & Lardner

[57] ABSTRACT

An Anthurium plant named Pink Frost, particularly characterized by the combined characteristics of pink flowers which are held among and above the foliage, symmetrical habit, many branches, dark green shiny leaves, tolerance to heat and a common disease (Xanthomonas), and rapid growth habit.

2 Drawing Sheets

The present invention comprises a new and distinct cultiver of Anthurium, botanically known as *Anthurium hybrid*, and referred to by the cultivar name Pink Frost.

The new cultivar is a product of a planned breeding program carried out in Coral Gables, Fla. The seedling is a result of a cross made in Coral Gables by inventor Richard J. Button between unidentified parents. The new cultivar was discovered and selected by inventor Ann E. Lamb from the progeny of the stated cross. The new cultivar was asexually reproduced as performed at Palmdale, Fla. by inventor Ann E. Lamb in August 1991 by tissue culture to increase the number of plants for evaluation, which evaluation has demonstrated the stability of the combination of characteristics of Pink Frost from generation to generation.

The following observations, measurements and values describe plants grown in Zolfo Springs, Fla. under shade house conditions which closely approximate those generally used in horticultural practice. The phenotype may vary somewhat with variations in environment such as temperature, light intensity and daylength, without, however, any variation in the genotype.

The following traits have been repeatedly observed to be characteristics which in combination distinguish Pink Frost from other Anthuriums of the same general type, for example, the well known cultivar Lady Jane (not patented).

1. The flowers are claret rose pink with a white spadix.
2. The plant has an attractive symmetrical growth habit.
3. The leaves are glossy dark green, and durable.
4. The flowers are held both above and among the leaves.
5. The plant is free branching.
6. The plant is tolerant to heat.
7. The plant is field tolerant to a common greenhouse disease, Xanthomonas.
8. The plant is a rapid grower.

In the following description, color references are made to the Royal Horticultural Society Colour Chart.

The accompanying color photographic drawings show typical inflorescence and foliage characteristics in Pink Frost, with colors being as nearly true as possible with illustrations of this type.

Sheet 1 is a top perspective view of a plant of Pink Frost grown in a 20.4 cm pot approximately 54 weeks after planting a 20 week old liner obtained by tissue culture and grown under appropriate growing conditions.

Sheet 2 comprises a closeup view of the inflorescence.

Origin: Seedling of unknown parentage.

Classification: *Anthurium hybrid* cv. Pink Frost.

Propagation: Asexual production either by tissue culture or division.

Plant: When grown in a 20.4 cm pot from a liner after 54 weeks under appropriate growing conditions, a plant of Pink Frost will reach typical mature size of approximately 35 cm to 51 cm in height and approximately 61 cm to 78 cm in width.

Leaves:

*Form.*—The leaf blade is deltoid with an acuminate tip and a truncate base. The margins are entire. The midrib tends to curve upward over the length of the leaf. The leaf blade tends to be somewhat wavy over the width of the leaf.

*Size.*—Leaf blades of a mature sized plant are approximately 24.7 cm to 25.2 cm in length and approximately 15.0 cm to 17.6 cm in width.

*Petiole.*—The petiole is approximately 22.8 cm to 29.4 cm in height from the base of the petiole to the base of the leaf blade on the primary shoot. Secondary shoots are somewhat smaller depending on the age of the shoot. The petiole is approximately 4 mm to 5 mm in diameter just below the geniculum, and is curved at the geniculum.

*Petiole wings.*—Petiole wings are approximately 3.3 cm to 4.1 cm in length and approximately 3.0 mm to 4.5 mm in width at their midpoint. The tips of the petiole wings are obtuse. There is approximately 16.5 to 21.8 cm between the top of the wing and the base of the geniculum.

*Geniculum.*—The geniculum is approximately 31 mm to 39 mm in length, approximately 5 mm to 6 mm in diameter, and is curved. The color is 144A. There is no space between the top of the geniculum and the base of the leaf blade. The geniculum is prominent.

*Veins.*—Veins are sunken, with the leaf blade being slightly convex between veins on the upper surface. The midrib protrudes from the upper leaf surface for approximately ⅔ the length of the leaf. Well defined primary veins radiate out from the juncture of the petiole and the leaf. Veins stand out prominently on the lower side. There are approximately 6 primary veins on each leaf.

*Lobes.*—The leaf has two lobes extending past the petiole. The distance from the petiole/leaf juncture to the highest point on the lobes is approximately 5.0 cm to 6.0 cm.

*Color.*—Upper surface: 139A. Lower surface: Greener than 138B. Midrib, upper surface: 144A. Midrib, lower surface: 144A-B. Petiole: 144A. Petiole wing: 144A.

Inflorescence:

*Immature spathe.*—The spathe is tightly rolled around the spadix and extrudes from the petiole sheath. The spathe is fully open about when the pedicel is fully elongated, approximately 34 cm to 41 cm above the soil surface.

*Mature spathe.*—Size: The flattened spathe is approximately 8.3 cm to 10 cm long approximately 6.6 cm to 8.0 cm in width, and 4–9 mm in depth. Color, fully open: Upper surface: 50B-C. Lower surface: 51C. Color, faded: Upper surface: 54B-C. Lower surface: 54D with spots of green 145B on top and base of spathe. Arrangement: The spathe stands up on straight wiry pedicels and opens vertically above or among the leaves. Shape: The spathe is deltoid with a cuspidate apice that is hooked upward at the tip. It is slightly cupped when first open. Flowering time: After approximately 13–14 months for an untreated plant grown from a liner, and depending on the seasons, approximately 5 to 11 blossoms will be present. Smaller blossoms may occur on less mature growth. Approximately 1–3 flowers will be present at first flowering approximately 4 to 5 months after planting.

Reproductive organs:

*Spadix.*—Size: Approximately 5.0 cm to 5.4 cm in height and approximately 6 mm to 8 mm in width. Color: When the spathe unrolls, the spadix is whiter than 19D, with 49B at the tip, gradually changing to 145B before senescing. Stamens: Anthers and filaments are not clearly visible. Pollen: White in color. Pistil: Lighter than 19D, protruding between the staminate flowers, firmly fixed to the main axil. The pistilate flowers extend approximately 0.5 mm beyond the staminate flowers.

*Roots.*—White fleshy roots with fine laterals. Roots initiated above the soil have a light pink cast.

GENERAL OBSERVATIONS

Pink Frost has claret rose pink flowers with a contrasting white spadix. The flowers are held both above and among the foliage. The leaves are shiny, dark green and durable. Compared to other Anthuriums of this type (Lady Jane) there are many axillary shoots. The plant habit is symmetrical. Pink Frost is tolerant to heat, a common greenhouse disease (Xanthomonas), and is a rapid grower. These combined features make Pink Frost a unique new cultivar.

We claim:

1. A new and distinct cultivar of Anthurium plant named Pink Frost, as illustrated and described.

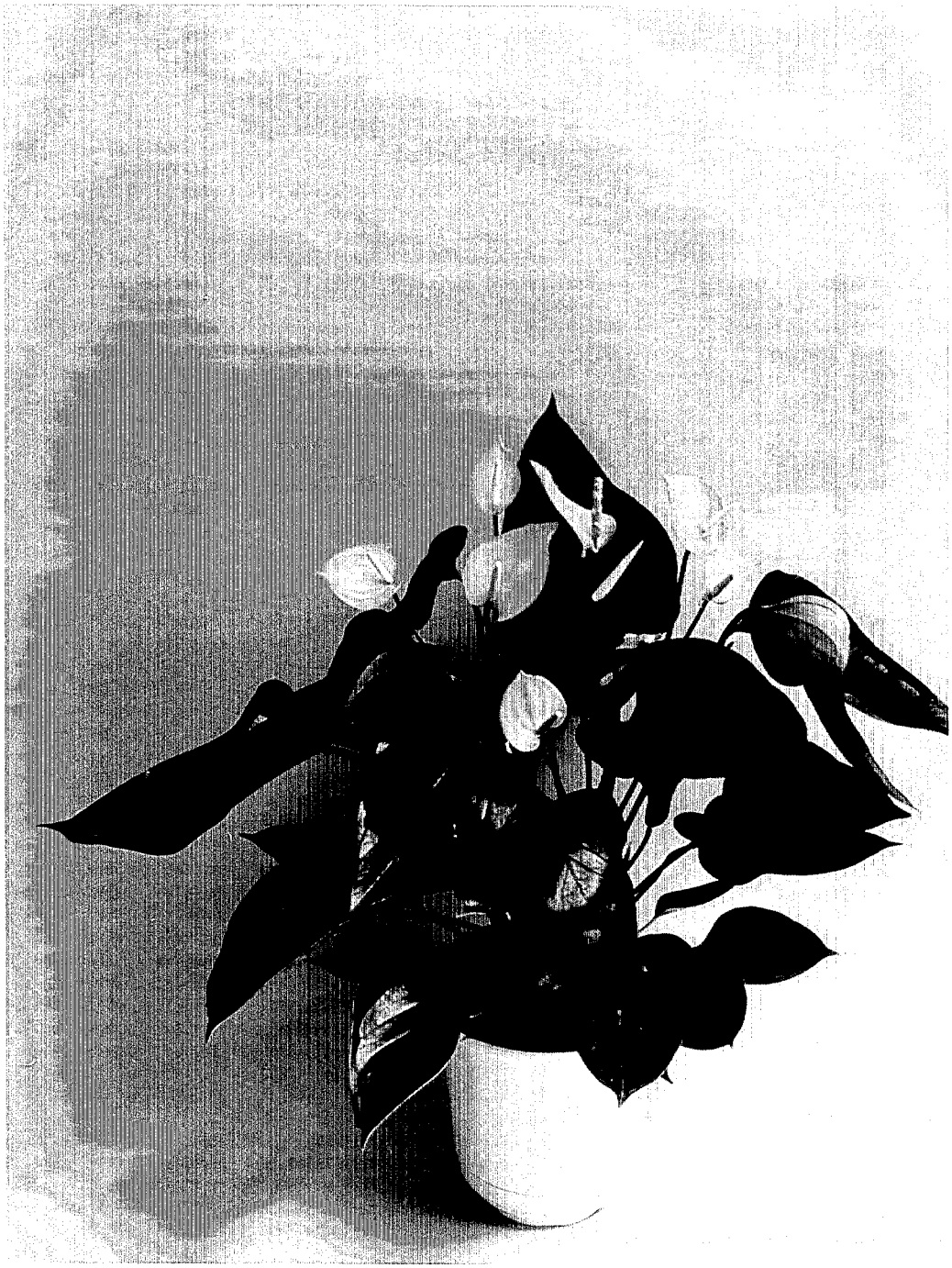

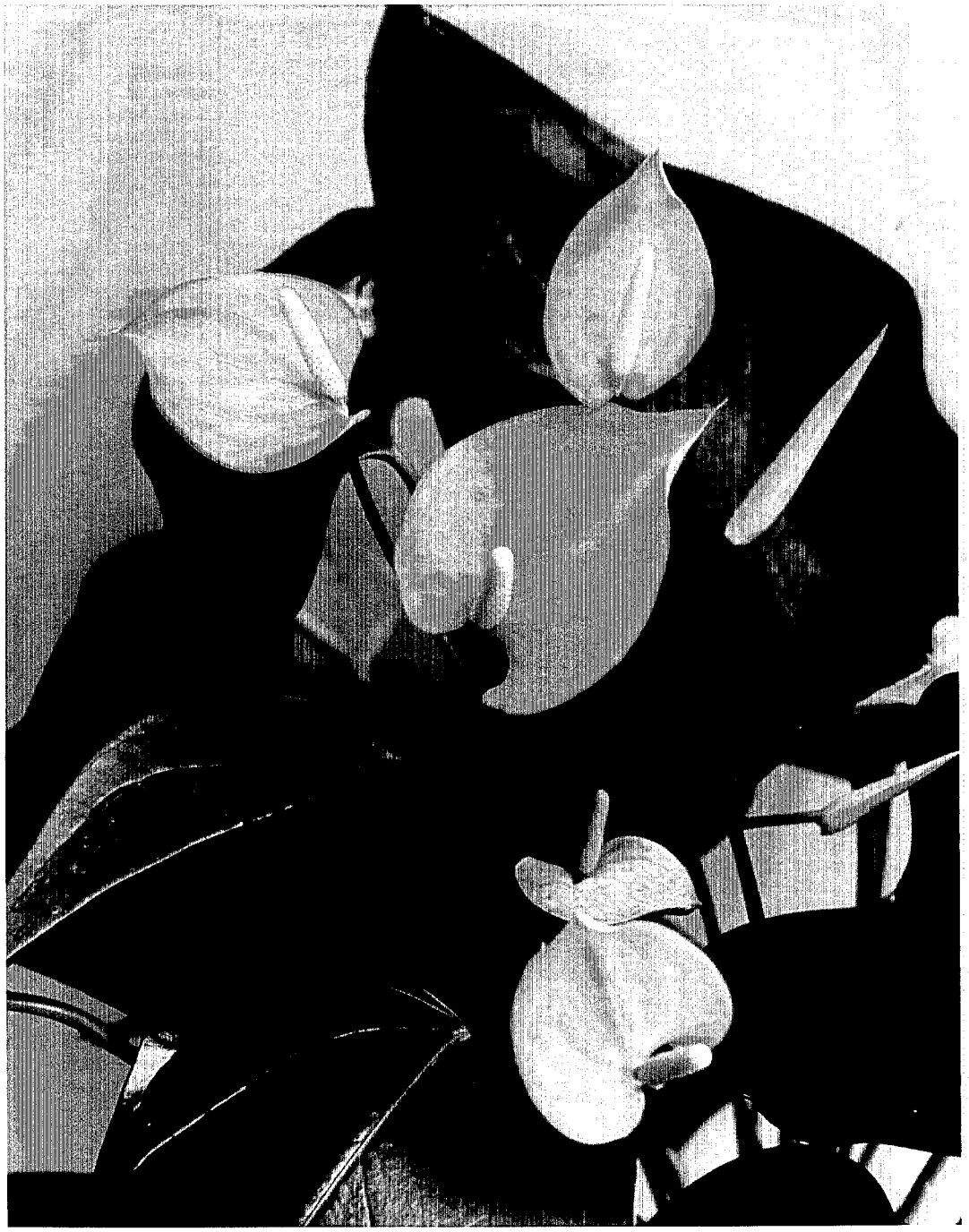

* * * * *